United States Patent [19]
Weber et al.

[11] Patent Number: 5,554,519
[45] Date of Patent: Sep. 10, 1996

[54] PROCESS OF PREPARING GENISTEIN

[75] Inventors: J. Mark Weber, Chicago; Andreas Constantinou, Naperville; Paul E. Hessler, Berwyn, all of Ill.

[73] Assignee: FermaLogic, Inc., Chicago, Ill.

[21] Appl. No.: 512,192

[22] Filed: Aug. 7, 1995

[51] Int. Cl.$^6$ .................................................. C12P 17/06
[52] U.S. Cl. ........................ 435/125; 435/252.1; 435/822
[58] Field of Search ................................ 435/125, 252.1, 435/822

[56] References Cited

U.S. PATENT DOCUMENTS

| | | | |
|---|---|---|---|
| 2,653,899 | 9/1953 | Bunch et al. | 435/70 |
| 3,974,184 | 8/1976 | Umezawa et al. | |
| 4,366,248 | 12/1982 | Zienllik | 435/125 |
| 4,960,908 | 10/1990 | Ito et al. | 549/403 |
| 5,070,015 | 12/1991 | Petuch et al. | 435/42 |
| 5,124,258 | 6/1992 | Arison et al. | 435/119 |
| 5,140,042 | 8/1992 | Arison et al. | 514/450 |
| 5,141,746 | 8/1992 | Fleury et al. | 424/195.1 |
| 5,141,926 | 8/1992 | Weber et al. | 514/79 |
| 5,192,671 | 3/1993 | Arison et al. | 435/101 |
| 5,320,949 | 6/1994 | Shen | 435/68.1 |

OTHER PUBLICATIONS

Akiyama, T., J. Ishida, S. Nakagawa, H. Ogawara, S. Watanabe, N. Itoh, M. Shibuya, and Y. Fukami. 1987. *Genistein, A Specific Inhibitor Of Tyrosine–Specific Protein Kinases*, J. Biol. Chem. 262, 5592–5595.

Akiyama, T., H. Ogawara. 1991. *Use And Specificity Of Genistein As Inhibitor Of Protein Tyrosine Kinases*. Methods Emzymol. 201:362–371.

Aoyagi, T.; T. Hazatok, M. Kumagai, M. Hamada, T. Takeuchi, H. Umezawa. 1975. *Isoflavone Rhamunosides, Inhibitors of β–Galactosidase Produced by Actinomycetes*. J. Antibiot. 12:1006–1008.

Martin, P. W., K. B. Horowitz, D. S. Ryan, and W. L. McGurie. 1978. *Phytoestrogen Inteaction With Estrogen Receptors In Human Breast Cancer Cells*. Endocrinol. 103:1860–1867.

Messina, M. and S. Barnes. 1991. *The Role Of Soy Products In Reducing The Risk Of Cancer*. J. Natl. Cancer Inst. 83:541–545.

Nakayama, O.; M. Yagi, M. Tanaka, S. Kiyoto, I. Uchida, M. Hashimot, M. Okuhara, and M. Kohsaka. 1990. *WS–7528, A New Isoflavanone With Estrogen Activity Isolated From Streptomyces Sp. No. 7528*. The Journal of Antibiotics, 11:1394–1402.

Ogawara, H.; T. Akiyama, J. Ishida, S. Watanabe, and K. Suzuki. 1985. *A Specific Inhibitor For Tyrosine Protein Kinase From Pseudomonas*. J. Antibiot. 39:606–608.

Okura, A., H. Arakawa, H. Oka, T. Yoshinari, and Y. Monden. 1988. *Effect Of Genistein On Topoisomerase Activity And On The Growth Of [VAL 12] Ha–ras–Transformed NIH 3T3 Cells*. Biochem. Biophys. Res. Commun. 157:183–189.

Olah, A. F. and R. T. Sherwood. 1972. *Glycosidase Activity and Flavonoid Accumulation in Alfalfa Infected by Aschochyta Imperfecta*. Phytopathology 63:739–742.

Perez–Pons J. A.; A. Cayetano, X. Rebordosa, J. Lloberas, A. Guasch, E. Querol. 1994. *A Beta–Glucosidase Gene (Bgl3) From Streptomyces Sp. Strain QM–B814. Molecular Cloning, Nucleotide Sequence, Purification And Characterization Of The Encoded Enzyme, A New Member Of Family 1 Glycosyl Hhydrolases*. Eur. J. Biochem. 223:557–565.

Sarlaslani, F. S.; and D. A. Kunz, 1986. *Induction Of Cytochrome P–450 In Streptomyces Griseus*. Biochemical and Biophysical Research Communications, 141, 2:405–410.

Schliemann, W. β–D–Glucosidasen (EC 3.2.1.21) *der Mikroorganismen*. Die Pharmazie. 1983. 38:287–303.

Uckun, F. M., W. E. Evans, C. J. Forsyth, K. G. Waddick, L. T. Ahlgren, L. M. Chelstrom, A. Burkhardt, J. Bolen, and D. E. Myers. 1995. *Biotherapy Of B–Cell Precursor Leukemia By Targeting Genistein To CD19–Associated Tyrosine Kinases*. Science 267:886–891.

Walter, E. D. 1941. *Genistin (An Isoflavone Glucoside) And Its Aglucone, Genistein, From Soybeans*. 63: 3273–3275.

Wright, R. M.; M. D. Yablonsky, Z. P. Shalita, A. K. Goyal, and D. E. Eveleigh. 1992. *Cloning Characterization, And Nucleoside Sequence Of A Gene Encoding Microbispora Bispora BglB, A Thermostable Beta–Glucosidase Expressed In Escherichia Coli*. Appl. Environ. Microbiol. 58:3455–3465.

Yam, L. T., C. Y. Li, and W. H. Crosby. 1971. *Cytochemical Identification Of Monocytes And Granulocytes*. Am. J. Clin. Pathol. 55:283–290.

Baker, W. and R. Robinson, 1928. *Synthetical Experiments in the IsoFlavone Group. Part III. A synthesis of Genistein*.

Castle, L. A.; K. D. Smith, and R. O. Morris. 1992. *Cloning And Sequencing Of An Agrobacterium Tumefaciens β–Glucosidase Gene Involved In Modifying A Vir–Inducing Plant Signal Molecule*. Journal of Bacteriology, 5:1478–1486.

Chimura, H. T. Sawa, Y. Kumada, H. Naganawa, M. Matsuzaki, T. Takia, M. Hamada. T. Takeuchi, and H. Umezawa. 1975. *New Isoflavones, Inhibiting Catechol–O–Methyltransferase, Produced By Streptomyces*. J. Antibiot. 28:619–626.

Collins, S. J., A. Bonder, R. Ting. and R. C. Gallo. 1980. *Induction Of Morphological And Functional Differentiation Of Human Promyelocytic Leukemia Cells (HL–60) By Components Which Induce Differentiation Of Murine Leukemia Cells*. Int. J. Cancer 25:213–218.

(List continued on next page.)

Primary Examiner—Herbert J. Lilling
Attorney, Agent, or Firm—Dressler, Goldsmith, Shore & Milnamow, Ltd.

[57] ABSTRACT

The present invention provides a process of preparing the isoflavone genistein. Genistein is prepared by fermenting the bacteria *Saccharopolyspora erythraea* in the presence of a soy-based substrate. A process of recovering genistein from a bacterial fermentation medium using alkaline, organic solvent extraction is also provided.

11 Claims, No Drawings

OTHER PUBLICATIONS

Constantinou, A., K. Kiguchi, and E. Huberman. 1990. *Induction Of Differentitaion And DNA Strand Breakage In Human HL–60 And K–562 Leukemia Cells By Genistein.* Cancer Res. 50:2618–2624.

Constantionou, A., and E. Huberman. 1995. *Genistein As An Inducer Of Tumor Cell Differentiation: Possible Mechanism Of Action.* Proc. Soc. Exper. Biol. Med. 208:109–115.

Constantinou, A., R. G. Mehta, C. Rao, K. V. N. Vaughn, and R. C. Moon. 1995. *Plant Flavonoids As DNA Topoisomerase Antagonists And Poisons: Structure–Activity Relationships.* J. Natural Products 58:217–225.

Funayama, S. Y. Anraku, A. Mita, K. Komiyama, and S. Omura. 1989. *Structural Study Of Isoflavonoids Possessing Antioxidant Activity Isolated From The Fermentation Broth Of Streptomyces Sp.* J. Antibiot. 42:1350–1355.

Gamba–Vitalo, C., O. C. Blair, S. R. Keyes, and A. C. Sartorelli. 1986. *Differentiation Of WEHI–3B $D^+$ Monomyelocytic Leukemia Cells By Retinoic Acid And Aclacinomycin A.* Cancer Res. 46:1189–1194.

Ganguly, A. K. and O. Z. Sarre. 1970. *Genistein And Daidzein, Metabolities Of Micromonospora Halophytica.* Chemistry and Industry (Feb.) p. 201.

Grisebach, H. 1967. *Biosynthesis Of Flavonoids And Related Products.* In Biosynthetic Patterns in Microorganisms and Higher Plants (Author, H. Grisebach). John Wiley and Sons, Inc., New York. pp. 1–31.

Hazato, T., H. Naganawa, M. Kumagai, T. Aoyagi, and H. Umezawa. 1979. *β–Galactosidase–Inhibiting New Isoflavnoids Produced by Actinomycetes.* J. Antibiot. 32:217–222.

Hay, G. W.; D. W. S. Westlake, and F. J. Simpson. 1961. *Degradation of Rutin by Aspergillus Flavus. Purification and Characterization of Rutinase.* Can. J. Microbiol. 7:921–932.

Hudson, A. T. and R. Bentley. 1969. *The Isolation Of Isoflavorable From Bacteria.* Chemical Communications, (J. Chem. Soc. –D). pp. 830–831.

Kiguchi, K., A. I. Constantinou, and E. Huberman. 1990. *Genisten–Induced Cell Differentiation And Protein Linked DNA Strand Breakage In Human Melanoma Cells.* Cancer Communications 2:271–278.

Komiyama, Kanki; S. Funayama, Y. Anraku, A. Mita, Y. Takahashi, and S. Omura. 1989. *Isolation Of Isoflavonoids Possessing Antioxidant Activity Isolated From The Fermentation Broth Of Streptomyces Sp.* J. Antibiotic 42:1344–1349.

Kondo, H.; S. Nakajima N. Yamamoto. A. Okura, F. Satoh. H. Suda, M. Okanishi, and N. Tanaka. 1990. *BE–14348 Substances, New Specific Estrogen–Receptor Binding Inhibitors. Production, Isolation, Structure Determination, And Biological Properties.* J. Antibiotics 43:1533–1542.

MacDonald, I. A.; R. G. Bussard, D. M. Hutshison, and L. V. Holdeman. 1984. *Rutin–Induced β–Glucosidase Activity in Streptococcus Faecium VGH–1 and Streptococcus sp. Strain FRP–17 Isolated From Human Feces: Formation Of The Mutagen, Quercetin, From Rutin.* Applied and Environmental Microbiology, 47:350355.

Markovits, J. C. Linassier, P. Fosse, J. Couprie, J. Pierre, A. Jacquemin–Sablon, J. M. Saucier, J. B. LePecq. A. K. Larsen. 1989. *Inhibitory Effects Of The Tyrosine Kinase Inhibitor Genistein On Mammalian DNA Topoisomerase II.* Cancer Res. 9:5111–5117.

PROCESS OF PREPARING GENISTEIN

TECHNICAL FIELD OF THE INVENTION

The field of this invention is genistein production. More particularly, the field of this invention is genistein production using fermentation of the bacteria *Saccharopolyspora erythraea* on a soy-based substrate.

BACKGROUND OF THE INVENTION

Genistein is an isoflavone. Isoflavones are a subclass of flavonoids, natural products typically isolated in glycosylated form from plants. The aglycone is the biologically active form that has the most medical and commercial interest.

The glycosylated form of genistein is known as genistin. The preparation of genistein must include a step in which the core isoflavone structure (genistein) is separated from the glucose moiety. Genistin, which is found in soybeans, is convened to the biologically active form, genistein, through the action of a beta-glucosidase enzyme.

Demand for genistein is expected to increase significantly in the near future. Genistein is becoming an established research tool as an inhibitor of protein tyrosine kinase, an enzyme involved in increased cell proliferation. Protein tyrosine kinase (PTK), is one of genistein's well studied biological targets. PTK is known to give cells a proliferative advantage. A variety of oncogenes of the Src family have been shown to have tyrosine kinase activity. Genistein is a PTK inhibitor. Genistein inhibited the PTK activities of EGF-receptor and pp60v-src with an ID50 of 6 and 7 µg/ml respectively in experiments using purified components, but in intact A431 cells 40 µg/ml were required to inhibit the cellular phosphotyrosine levels. Genistein is reported to be an inhibitor of eukaryotic DNA topoisomerase (topo) I and II.

Genistein is used as a chemopreventive agent in animal studies, is required for clinical trials as a dietary supplement; and likely has application as a chemotherapeutic agent when coupled to anti-tumor specific antibodies.

Populations consuming soybeans show reduced incidence of breast, colon, and prostate cancer. Initial animal studies suggested that two isoflavones, genistein and daidzein, may be the active ingredients of soybeans that function as chemopreventive agents. Genistein injected into neonatal rats reduces dimethylbenz(a)anthracene (DMBA)-induced mammary tumor induction by about 50%. Either genistein or daidzein provides some protection against N-methyl N-nitrosurea (MNU)-induced mammary tumors in rats. Although genistein was effective in reducing both the tumor incidence and multiplicity, daidzein reduced only multiplicity in the later studies.

Currently genistein is being tested by the National Cancer Institute against colon carcinogenesis, as part of the Chemoprevention Screening Program, and early results show effectiveness against colon papillomas. Clinical trials to identify the metabolism and pharmacokinetics of genistein (phase I) are also being currently performed.

A recent study identified genistein as a potent antitumor agent (when coupled with antitumor specific antibodies) against colon carcinogenesis of human B-cell leukemia in immunodeficient mice. The B43-genistein immunoconjugate at less than one-tenth the maximum tolerated dose killed more than 99% of human leukemia cells. The postulated mechanism of genistein's action in this study was that of PTK inhibitor.

Because of the potential clinical use of genistein as a chemopreventive and/or chemotherapeutic agent it is becoming essential to produce this isoflavone and some of its promising structural analogs in larger quantities and to reduce its price. Genistein is currently expensive to produce using current technology. Chemically synthesized genistein or genistein extracted from soybeans currently can cost up to $5,000 a gram. However, the compound is not produced routinely in kilogram quantities at present.

The present invention provides an inexpensive process for the large scale production of genistein wherein *Saccharopolyspora erythraea*, the organism that is used in the commercial production of erythromycin, is fermented on a soy-based fermentation medium.

BRIEF SUMMARY OF THE INVENTION

The present invention provides a process of preparing genistein comprising fermenting the bacteria *Saccharopolyspora erythraea* on a soy-based substrate. The genistein that is formed by this fermentation is then recovered from the fermentation medium. In accordance with this process, *Saccharopolyspora erythraea* is cultured for a period of time and under culture conditions sufficient for genistein formation. Suitable culture conditions include a temperature of from about 10° C. to about 50° C. in an aqueous, oxygenated medium having a pH value of from about 4.0 to about 9.0, which medium contains organic nutrients, vitamins and inorganic salts sufficient to maintain *Saccharopolyspora erythraea* viability. More preferably, the temperature is from about 20° C. to about 30° C. and the medium has a pH value of from about 6.0 to about 8.0. A preferred time of fermentation is from about 20 hours to about 250 hours.

Genistein is recovered from the fermentation or culture medium by extraction in a water-immiscible organic solvent at a pH value of from about 8.0 to about 11.0. Preferably, the pH value is from about 9.0 to about 10.0. A preferred organic solvent is ethyl acetate.

In another aspect, the present invention provides a process of recovering genistein from a bacterial fermentation medium comprising extracting genistein from the medium in a water-immiscible organic solvent at a pH value of from about 8.0 to about 11.0 and, preferably from about 9.0 to about 10.0. A preferred organic solvent is the same as set forth above. In a preferred embodiment, the bacterial fermentation is a fermentation of *Saccharopolyspora erythraea*.

DETAILED DESCRIPTION OF THE INVENTION

I. The Invention

The present invention provides an inexpensive, large-scale process for preparing the isoflavone genistein. That process is based on the surprising discovery that genistein is produced during fermentation of the bacteria *Saccharopolyspora erythraea*, which is used in the commercial production of the antibiotic erythromycin. The present inventors have further discovered that genistein is recovered from that fermentation along with erythromycin during alkaline, organic solvent extraction.

Typically, industrial fermentations are designed for the production of a single compound of interest such as an antibiotic. This compound is traditionally a biosynthetic product of the microorganism, referred to as a secondary metabolite. The growth medium is thought of strictly as a source of carbon and nitrogen and other necessary nutrients for the growth of the organism and production of the natural product from primary metabolic precursors produced by the microorganism.

The present disclosure that genistein is produced in the erythromycin fermentation enables one to recognize that the growth medium itself can be a significant source of additional products which can be used to add value to the overall fermentation.

The process of the present invention has advantages over other means for preparing genistein. When compared to chemical synthetic procedures, the present process is more efficient, less costly and capable of producing genistein in large-scale quantities. When compared to procedures involving the extraction of genistein from soy beans per se, the present process has the advantage of selectively producing genistein as opposed to its relatively inactive glycosylated precursor, genistin. This is true because *Saccharopolyspora erythraea* produces and secretes, during fermentation a unique form of a beta-glucosidase, which enzyme catalyses the removal of the glucose from genistin to form genistein.

This is highly advantageous not only because it is genistein, and not genistin, that is the biologically active compound but also because genistein (not genistin) is extractable from the fermentation medium broth under the same conditions (e.g., alkaline pH and organic solvent) that are used to recover erythromycin. It is surprising and unexpected that the same solvent and pH can be used to extract both genistein and erythromycin.

II. Process of Preparing Genistein

The present invention therefore provides a process of preparing genistein comprising fermenting *Saccharopolyspora erythraea* on a soy-based substrate. As used herein, the term "fermenting" or its grammatical equivalents, refers to the process of culturing *Saccharopolyspora erythraea* in a medium that provides nutrients, vitamins and inorganic salts sufficient to maintain viability of the bacteria such that it will assimilate medium constituents (e.g., carbon and nitrogen) and produce erythromycin. Suitable media and conditions for bacterial fermentation are well known in the art. By way of example, U.S. Pat. No. 2,653,899, the disclosure of which is incorporated herein by reference, discloses the fermentation of *Streptomyces erythreus* so as to produce erythromycin.

The fermentation of *Saccharopolyspora erythraea* to produce genistein in accordance with the present invention comprises culturing *Saccharopolyspora erythraea* for a period of time and under culture conditions sufficient for genistein formation. Culture conditions include, as is well known in the art, temperature and composition of the culture medium such as pH, nutrient levels, osmolality and the like.

As is also well known in the art, a preferred medium is an aqueous medium that is oxygenated. That medium contains assimilatable sources of carbon and nitrogen. Exemplary sources of carbon include, but are not limited to, carbohydrates such as starch, sugars (e.g., arabinose, fruetose, galactose, maltose, sucrose) and organic salts (e.g., sodium acetate, sodium titrate, sodium malate). One of skill in the art can readily determine the optimum concentrations of such carbon sources in the culture medium.

The nitrogen source of the culture medium must include a soy-based substrate. As used herein, the term "soy-based substrate" refers to a substrate of any form that includes or is derived from soybeans. That soy-based substrate can be soybean meal, soybean flour, soybean oil, soybean grits, and the like. Such soy-based substrates are commercially available. Exemplary substrates and their commercial source are set forth hereinafter in the Examples.

The culture or fermentation medium can contain assimilatable nitrogen sources in addition to the soy-based substrate. Exemplary such additional nitrogen sources include, but are not limited to, corn steep, amino acid mixtures, casein, peptones and the like.

The culture medium further comprises inorganic salts that serve to provide any necessary cofactors for cell viability, genistein production and erythromycin production as well as for maintaining osmolarity within normal limits. Typically, as is well known in the art, those salts include sodium, potassium, chloride, magnesium calcium and the like. One of ordinary skill can readily determine the optimum levels of such inorganic salts. The pH of the culture medium is maintained at a suitable level for fermentation. A preferred medium pH value is from about 4.0 to about 9.0 and, more preferably from about 6.0 to about 8.0. Medium pH can be maintained with the use of buffers as needed.

As is well known in the art, fermentation can be performed over a wide range of temperatures. In a preferred embodiment, fermentation temperature is from about 10° C. to about 45° C. and, more preferably from about 20° C. to about 40° C.

Fermentation is maintained for a period of time sufficient for genistein formation. That time will vary, as is well known in the art, on culture conditions, concentration of the bacteria and the like. Under culture conditions such as set forth above, suitable times typically range from about 20 hours to about 250 hours.

Genistein, formed from the fermentation of *Saccharopolyspora erythraea* in accordance with a process of the present invention is recovered from the fermentation or culture medium. Any means of recovering genistein can be used. It is preferred, however, to recover genistein using conditions similar to those used to recover erythromycin from the same medium. In accordance with this preferred embodiment and, as set forth below, genistein is recovered from the medium using organic solvent extraction at an alkaline pH.

III. Process of Recovering Genistein

In another aspect, therefore, the present invention provides a process of recovering genistein from a bacterial fermentation medium that contains genistein, the process comprising extracting the genistein from the fermentation medium in an organic solvent at a pH value of from about 8.0 to about 11.0.

In accordance with the process, the fermentation medium is adjusted to an alkaline pH by the addition of an alkalinizing salt. The alkaline pH can range from a pH value of about 8.0 to a pH value of about 11.0. More preferably, the pH value is from about a pH value of 9.0 to a pH value of about 10.0 and, even more preferably a pH value of about 9.5.

Any alkalinizing salt can be used so long as that salt does not interfere with the isolation and biological stability of genistein. An exemplary and preferred alkalinizing salt is sodium hydroxide.

The alkalinized fermentation medium is then extracted with an organic solvent. That organic solvent is preferably water immiscible. Any organic solvent can be used so long as that solvent does not interfere with the isolation or biological stability of genistein. Means for determining suitable such solvents are well known in the art and within the knowledge of one of ordinary skill in the art. Exemplary and preferred organic solvent include, but are not limited to alkyl esters of fatty acids (e.g., ethyl acetate, amyl acetate) chlorinated hydrocarbons (e.g., chloroform, ethylene dichloride), ethers, ketones and alcohols (e.g., butanol, amyl alcohol). Particularly preferred organic solvents are alcohols such as n-butanol and alkyl fatty acid esters such as amyl acetate and ethyl acetate.

Genistein is isolated and purified from the organic solvent extract (solvent fraction) using standard procedures well known in the art. By way of example, the solvent fraction is extracted with acidified water to remove the erythromycin: the genistein stays with the organic fraction and the erythromycin is extracted into the water fraction. Genistein is then isolated from the solvent using, typically, solvent evaporation and high pressure liquid chromatography (HPLC). A detailed description of the recovery of genistein using a process of the present invention is set forth hereinafter in the Example.

The following Example illustrates preferred embodiments of the present invention and is not limiting of the specification and claims in any way.

EXAMPLE 1

Microbial Production Of Genistein

A variety of bacterial strains were studied for their ability to produce genistein. Three of those strains (Actinomyeete bacteria) were reported to produce isoflavones and were purchased from the American Type Culture Collection (ATCC). Those three strains were *Streptomyces roseolus* (ATCC 31047), and *Micromonospora halophytica* (subspecies halophytica and nigra)(ATCC 27596 and ATCC 33088). Control strains (not reported to produce isoflavones) studied were *Saccharapolyspora erythraea* (ATCC 11635), an erythromycin producer, *Streptomyces lividans* TK21 (Hopwood et al., 1985), an actinorhodin producer, *Streptomyces hygroscopicus* (ATCC 29253) an ascomycin producer, *Streptomyces glaucescens* NRLL, a tetracenomycin producer, and *E. coli* DH5alpha.

Various strains were grown (fermented) in eight different media as set forth below.

1. AVMM (disclosed in U.S. Pat. No. 5,141,926, the disclosure of which is incorporated herein by reference)— asparagine (5 g), glucose (20 g), phosphate buffer at pH 7.0, essential vitamins (trace) and water (1 liter).

2. STB—Soytone Broth (Difco), yeast extract, NaCl (2.5 g), $CaCO_3$ (3.5 g), soluble starch (20 g) trace elements solution (0.25 ml) and water (1 liter).

3. SFB—SoyFluff Broth (Central Soya), yeast extract, NaCl (2.5 g), $CaCO_3$ (3.5 g), soluble starch (20 g) trace elements solution (0.25 ml) and water (1 liter).

4. SGB—NutraSoyaGrits (Cargill), yeast extract, NaCl (2.5 g), $CaCO_3$ (3.5 g), soluble starch (20 g) trace elements solution (0.25 ml) and water (1 liter).

5. G1—NZ amine (20 g), yeast extract (10 g), soluble starch (20 g), NaCl (2.5 g), $CaCO_3$ (3.5 g), trace elements solution (1.0 ml), 50% glucose solution (20 ml) and water (980 ml).

6. SGGP—Bactopeptone (4 g), yeast extract (4 g), glycine (2 g), $MgSO_4$ (0.5 g), 0.5M $KH_2PO_4$ (20ml), 50% glucose solution (20 ml) and water (960 ml).

7. SOD—tryptone (20 g), yeast extract (5 g), NaCl (0.5 g), 50% glucose solution (20 ml) and water (1 liter).

8. GM—beef extract (0.3%), tryptone (0.5%), dextrose (0.1%), soluble starch (2.4%) and water (1 liter).

Various bacterial strains were fermented in 50 ml of the various media at 30° C. for 96 hours. 20 mls of each fermentation media were then extracted with an equal volume of ethyl acetate. The solvent extract was evaporated to dryness, resuspended in about 100 microliters of ethyl acetate and subjected to HPLC. Extracts were examined for the presence of genistein and other isoflavones. The identification of genistein in the fermentation medium was made using standard gas chromatography/mass spectroscopy (GC/MS) procedures well known in the art.

None of the bacterial strains produced isoflavones when fermented in media that did not contain a soy-based substrate (i.e., AVMM, G1, SGGP, SOD, GM). These results were particularly surprising and unexpected with regard to those strains previously reported to produce isoflavones such as *Streptomyces roseolus* (ATCC 31047), and *Micromonospora halophytica* (subspecies halophytica and nigra)(ATCC 27596 and ATCC 33088). The present results bring into question the claims of U.S. Pat. No. 3,973,608 to Umezawa et al., which discloses that *Streptomyces roseolus* produces isoflavone during fermentation. Although that patent disclosed soy-based fermentation media as a suitable medium, other non-soy-based media were disclosed as being suitable for isoflavone production.

In contrast, genistein was produced when *Streptomyces roseolus*, and *Micromonospora halophytica* were fermented in media (STB, SFB and SGB) containing a soy-based substrate. Surprisingly, however, the fermentation of *Saccharapolyspora erythraea*, a strain not previously reported to produce isoflavones, also produced genistein in significant amounts when fermented in the presence of a soy-base substrate.

Extensive chemical analyses were performed on extracts from the *Streptomyces roseolus* and *Saccharapolyspora erythraea* fermentations. Briefly, purified material collected from HPLC was subjected to GC/MS analysis. The results showed that the material corresponding to the peak eluting at 15 min. was genistein. These findings were based on a comparison between the mass spectrum of material isolated from the medium and an authentic genistein standard.

Identity of the material was also checked against apigenin. Apigenin is the flavanone equivalent of genistein, having the same molecular weight and substitution pattern. Its mass spectrum is identical to that of genistein, except that the two compounds were distinguishable by the significantly longer elution time of apigenin (23:12) as opposed to genistein's elution time (20:53). The two compounds could also be easily separated by HPLC.

Genistein was not present in the uninoculated broth containing soy-based substrates and was not produced by fermentation of any bacteria in media without a soy-based substrate. These findings, taken together, show that genistein is not produced de novo by the bacteria. This finding is in direct contradistinction to previous teachings about the bacterial production of genistein (See, e.g.. U.S. Pat. No. 3,973,608).

Although not wishing to be bound by a particular theory, it is believed that genistein is produced during fermentation through the beta-glucosidae catalyzed removal of glucose from genistin present in the soy-based substrate. The beta-glucosidase is likely produced by *Saccharapolyspora erythraea* and secreted into the fermentation medium where it acts on genistin. Beta-glucosidases are a family of substrate-specific enzymes that serve to catalyze the removal of sugar moieties from particular substrates (See. e.g., Macdonald et al., *Applied and Environmental Microbiology,* 47:350, 1984). Although beta-glucosidases have been reported to occur in over 400 microorganisms, there are no reports of any beta-glucosidase activity in *Saccharapolyspora erythraea* (See, e.g.. Schliemann, *Pharmazie,* 38:1083, 1983). An examination of the report of Schliemann also reveals that there is no pattern to the particular type (i.e., substrate specificity) of beta-glucosidse amongst strains of bacteria. Thus, the observation that the fermentation of *Streptornyces griseus* on soybean meal resulted in genistein formation is, in no way, predictive of the present invention.

*Saccharopolyspora erythraea* produced 2.5 µg of genistein/ml of medium. The amount of glycosylated isoflavones (e.g., genistin) in North American soybeans is reported to be in the range of about 2.5 to 5 mg of glycosylated isofiavone/g dry soybean weight. Thus, a process of the present invention results in a production and recovery of genistein of about 25% of the genistein available. A typical industrial producer of erythromycin would use about 2,000 kg of crushed soybeans per tank (100,000 L) per week. This would potentially lead to the production of 5 kg of genistein per tank per week. A medium scale producer of erythromycin could have 10 dedicated tanks for erythromycin production, and would therefore be capable of producing 50 kg of genistein per week.

Genistein was efficiently extracted from *Saccharopolyspora erythraea* fermentations at a pH of 9.5. This is significant because erythromycin is also extracted from *Saccharopolyspora erythraea* fermentations at this elevated pH (See, U.S. Pat. No. 2,653,899, the disclosure of which is incorporated herein by reference). This means that in the industrial process genistein is co-purified with erythromycin, at least through the first step. Genistein remains in the ethyl acetate fraction after the erythromycin is further purified by back extraction into acidified water. Genistein in the solvent fraction is effectively highly purified in the solvent distillate. Thus, not only are large quantities of genistein produced, but it is in a highly purified and concentrated state.

The present disclosure that genistein can be extracted from a bacterial fermentation medium at an alkaline pH in an organic solvent is surprising in view of the structure of genistein as well as reported methods of genistein isolation and recovery. As is well known, genistein, chemical name 4',6,7-trihydroxyisofiavone, contains three hydroxyl groups. As is also well known, those hydroxyl groups tend to lose their hydrogen atoms and become negatively charged at alkaline pH values. As the pH increases, the solubility of genistein in an organic (non-polar) solvent would thus decrease and genistein should not be recoverable in that organic solvent. Indeed, all previous reports of genistein isolation in organic solvents utilized an acidified environment (See, e.g., Chimura et al., *The Journal of Antibiotics,* 28:619, 1975; U.S. Pat. Nos. 3,914,184 and 3,973,608; and Ogawara et al., *The Journal of Antibiotics,* 39:606, 1986).

What is claimed is:

1. A process of preparing genistein comprising fermenting *Saccharopolyspora erythraea* on a soy-based substrate and recovering the genistein.

2. The process of claim 1 wherein *Saccharopolyspora erythraea* is cultured for a period of time and under culture conditions sufficient for genistein formation.

3. The process of claim 2 wherein *Saccharopolyspora erythraea* is cultured at a temperature of from about 10° C. to about 45° C. in an aqueous, oxygenated medium having a pH value of from about 4.0 to about 9.0, which medium contains organic nutrients, vitamins and inorganic salts sufficient to maintain *Saccharopolyspora erythraea* viability.

4. The process of claim 3 wherein the temperature is from about 20° C. to about 30° C. and the medium has a pH value of from about 6.0 to about 8.0.

5. The process of claim 2 wherein the period of time is from about 20 hours to about 250 hours.

6. The process of claim 1 wherein genistein is recovered by extracting genistein from a fermentation medium in a water-immiscible organic solvent at a pH value of from about 8.0 to about 11.0.

7. The process of claim 6 wherein the pH value is from about 9.0 to about 10.0.

8. The process of claim 6 wherein the organic solvent is ethyl acetate.

9. A process of recovering genistein from a *Saccharopolyspora erythraea* fermentation medium comprising extracting genistein from the medium in an organic solvent at a pH value of from about 8.0 to about 11.0.

10. The process of claim 9 wherein the pH value is from about 9.0 to about 10.0.

11. The process of claim 9 wherein the organic solvent is ethyl acetate.

* * * * *